(12) United States Patent
Michot et al.

(10) Patent No.: US 6,254,797 B1
(45) Date of Patent: *Jul. 3, 2001

(54) IONIC CONDUCTING MATERIAL HAVING GOOD ANTICORROSIVE PROPERTIES

(75) Inventors: Christophe Michot, Grenoble; Michel Armand, Saint-Martin-d'Uriage; Jean-Yves Sanchez, St-Ismier, all of (FR); Yves Choquette, Sainte-Julie; Michel Gauthier, Varennes, both of (CA)

(73) Assignees: Centre National de la Recherche Scientifique, Paris (FR); Hydro-Quebec, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/274,883

(22) Filed: Mar. 23, 1999

Related U.S. Application Data

(63) Continuation of application No. 08/537,944, filed as application No. PCT/FR95/00343 on Mar. 21, 1995, now Pat. No. 5,916,475.

(30) Foreign Application Priority Data

| Mar. 21, 1994 | (FR) | 94.03276 |
| Mar. 21, 1994 | (FR) | 94.03277 |

(51) Int. Cl.$^7$ .................................................. C08L 7/02
(52) U.S. Cl. .................. 252/62.2; 423/383; 423/386; 423/365; 423/415.1; 423/472; 423/499.1; 423/499.2; 429/306
(58) Field of Search .......................... 429/306, 321, 429/307, 310, 324, 499.2; 252/62.2; 423/383, 386, 365, 415.1, 472, 499.1

(56) References Cited

U.S. PATENT DOCUMENTS

| 4,851,307 | * | 7/1989 | Armand et al. | 429/192 |
| 5,021,308 | * | 6/1991 | Armand et al. | 429/194 |
| 5,240,790 | * | 8/1993 | Chua et al. | 429/190 |
| 5,284,723 | * | 2/1994 | Hannecart et al. | 429/213 |
| 5,389,467 | * | 2/1995 | Herr et al. | 429/184 |
| 5,393,847 |   | 2/1995 | Alloin et al. . | |
| 5,514,493 | * | 5/1996 | Waddell et al. | 429/199 |
| 5,521,019 |   | 5/1996 | Allion et al. . | |
| 5,523,180 | * | 6/1996 | Armand et al. | 429/188 |
| 5,916,475 | * | 6/1999 | Michot et al. | 429/306 |

FOREIGN PATENT DOCUMENTS

| 5-283086 | * | 10/1993 | (JP) . |
| WO 93/26057 | * | 12/1993 | (WO) . |
| WO 97/23448 | * | 7/1997 | (WO) . |

OTHER PUBLICATIONS

Chemical Abstract No. 82:105835x, Apr. 1975.*
Ruff, John K, "The Imidodisulfuryl Ion," *Inorganic Chemistry*, vol. 1, No. 10, 1965, pp 1446–1449 (Month Unknown).*
Desmarteau et al, "Novel Layered Structures in Metal Salts of bis (sulfonyl)methanes," *Eur. J. Solid Inorg. Chem.*, 1991, pp 905–917 (Month Unknown).*

* cited by examiner

Primary Examiner—Laura Weiner
(74) Attorney, Agent, or Firm—Oblon, Spivak, McClelland, Maier & Neustadt, P.C.

(57) ABSTRACT

The invention relates to an ionically conductive material, to its preparation and to its uses.

Figure 1:
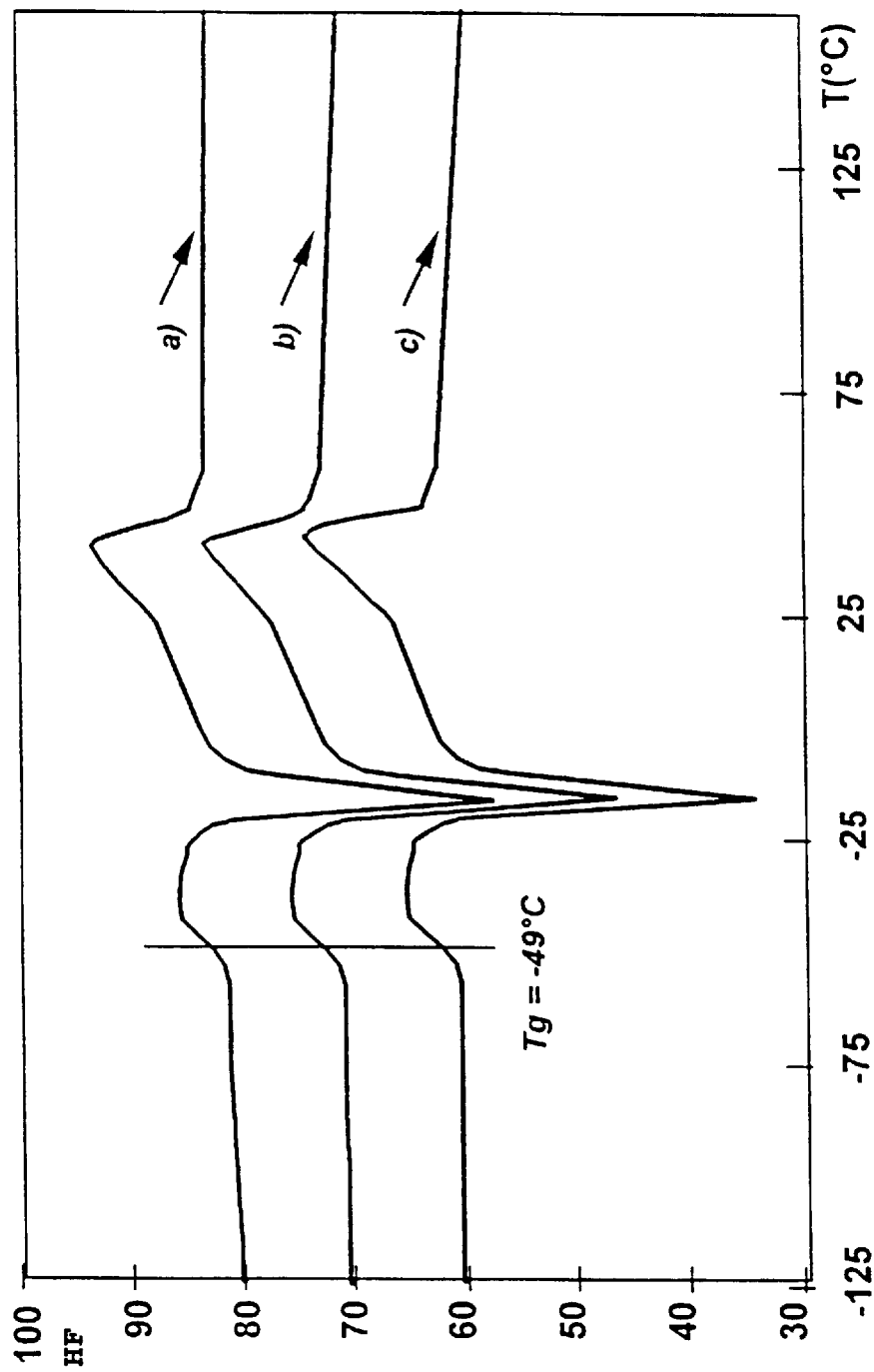

The material includes at least one ionic compound in solution in an aprotic solvent, chosen from the compounds $(1/mM)^+[(ZY)_2N]^-$, $(1/mM)^+[(ZY)_3C]^-$ and $(1/mM)^+[(ZY)_2CQ]^-$, in which Y denotes $SO_2$ or POZ, Q denotes —H, —COZ or Z, each substituent Z independently denotes a fluorine atom or an optionally perfluorinated organic group which optionally contains at least one polymerizable functional group, at least one of the substituents Z denoting a fluorine atom, and M denotes a cation.

Application to electrochemical generators, supercapacities, to the doping of polymers and to electrochromic devices.

39 Claims, 5 Drawing Sheets

IONIC CONDUCTING MATERIAL HAVING GOOD ANTICORROSIVE PROPERTIES

This application is a continuation of application Ser. No. 08/537,944 filed on Nov. 21, 1995, allowed, now U.S. Pat. No. 5,916,475 which was filed as International PCT application No. PCT/FR95/00343, filed Mar. 21, 1995.

The present invention relates to an ionically conductive material, to its preparation and to its uses.

Electrochemical systems for energy storage, for example batteries or supercapacities which operate with high elementary voltages, demand electrolytes which have an extensive range of stability. Such electrolytes are obtained by dissolving one or more solutes $(1/mM')^+X'^-$ in a dipolar liquid solvent, a solvating polymer or their mixtures. M' is a cation of valency m, such as a proton, a cation derived from a metal (for example Li, Na, K, Mg, Ca, Cu, Zn or La) or an organic cation such as an ammonium ion, a guanidinium ion, a phosphonium ion or a sulphonium ion. Ionic compounds $(1/mM')^+X'^-$ in which the anion $X'^-$ has a delocalized charge exhibit a high ionic conductivity. Among the $X'^-$ anions with a delocalized charge there may be mentioned $I^-$, $ClO_4^-$, $AsF_6^-$, $PF_6^-$, $R_FSO_3^-$, $(R_FSO_2)_2N^-$, $R^1CO(CF_3SO_2)_2C^-$ and $R^1SO_2(CF_3SO_2)_2C^-$, $R_F$ denoting a perfluoroalkyl radical or a perfluoroaryl radical, $R^1$ denoting a hydrogen atom, an alkyl radical, an oxaalkyl radical, an azaalkyl radical, an aryl radical, a perfluoroalkyl radical or a perfluoroaryl radical.

Although the abovementioned compounds may have high ionic conductivities, their use presents disadvantages. Iodide ions are easily oxidizable. Arsenic derivatives are toxic and perchlorates are explosive. Anions such as $PF_6^-$, capable of easily releasing a Lewis acid ($PF_6^- \rightarrow PF_5$) compromise the stability of the corresponding electrolytes via reactions causing the formation of electrophilic species of carbocation type.

Anions containing $R_FSO_2$— perfluorosulphonyl groups, in particular perfluorosulphonates $R_FSO_3^-$ and perfluorosulphonylimides $(R_FSO_2)_2N^-$, are stable and have low toxicity and the use of the corresponding ionic compounds has become generalized, especially for electrochemical generators including negative electrodes consisting of metallic lithium, a lithium alloy or a carbon-lithium intercalation compound. The preparation of these ionic compounds is, however, very costly, and the manufacture of compounds containing at least two perfluorosulphonyl groups very particularly so. Furthermore, these compounds have a high molecular mass and the mass fraction for a given molality in a solvent is large.

Compounds corresponding to the formula $(1/mM)^+$ $[FSO_2NSO_2F]^-$ are known where $(1/mM)^+=H^+$, $K^+$, $Cs^+$, $Rb^+$, $Ag^+$ and $(CH_3)_4N^+$ [J. K. Ruff, Inorg. Chem. 4, 1446, (1965)]. In general, a salt constitutes an electrolyte which is proportionally better the lower the basicity of its anion. The basicity of the $[FSO_2NSO_2F]^-$ anion is a priori higher than that of an $[R_FSO_2NSO_2R_F]^-$ anion in which $R_F$ is a perfluoroalkyl group, because of the retrocession of the free pairs of the fluorine on the sulphur atom. Many publications report the fact that the substitution of a perfluoroalkyl group for a fluorine atom in an organic compound which is acidic in nature decreases the strength of the acid. (G. Paprott & K. Seppelt, J. Am. Chem. Soc., 106, 4060 (1984); E. D. Laganis, D. M. Lema, J. Am. Chem. Soc., 102, 6634 (1984); F. J. Bordwell, J. C. Branca et al., J. Org. Chem., 53, 780, (1988)).

Furthermore, it is known that the fluorine atom of an F—S bond is particularly labile and especially hydrolysable in the presence of water or of nucleophilic bases. Because of these disadvantages the use of the acid $[FSO_2NSO_2F]H$ as protonic electrolyte in fuel cells is not recommended [M. Razak et al., J. Appl. Electrochem., 17 (5), 1057 (1987)]. On the other hand, the stability of the compounds $[R_FSO_2NSO_2R_F]H$ such as $H(CF_3SO_2)_2N$ or $H(CF_3SO_2NSO_2C_4F_9)$ has been demonstrated [M. Razak et al., op. cit.; M. Razak et al., J. Appl. Electrochem., 136, 385 (1989)].

It is also known that the compounds $H(FSO_2)_3C$ are hydrolysed spontaneously, whereas their homologues $(1/mM')^+[(R_FSO_2)_3C]^-$ have been proposed as electrolyte solutes for electrochemical generators. However, just as in the case of the imides, the molecular mass and the costs of manufacture of the compounds $[1/mM)^+[(R_FSO_2)_3C]^-$ are high and render their use of little interest.

JP-A-05 283 086 relates to a battery in which the electrolyte contains a cyclic ether as solvent and a salt including at least two $R_FSO_2$ groups, $R_F$ being a fluorine atom or a fluoroalkyl group. The use of salts containing two fluoroalkyl groups is described and illustrated by concrete examples relating to lithium bis(trifluoromethanesulphonyl) methanide. It is explained that a salt of the $(CF_3SO_2)_2NLi$ or $(CF_3SO_2)_3CLi$ type gives a conductivity which is higher when compared with a $CF_3SO_3Li$ salt owing to the fact that the presence of a single electron-withdrawing group on the atom adjoining the lithium atom in $CF_3SO_3Li$ increases the electron density on this atom, oxygen in this case, and therefore renders ionization, that is to say the release of $Li^+$, more difficult, whereas in a compound $(CF_3SO_2)_2NLi$ or $(CF_3SO_2)_3CLi$ the presence of two electron-withdrawing groups on the atom adjoining the lithium decreases the electron density on this atom and therefore promotes the release of the $Li^+$ ion. No information is given on salts including one or two $FSO_2$ groups. Furthermore, the conclusions drawn from the comparison between a compound $R_FSO_3Li$ and a compound $(R_FSO_2)_2NLi$ or $(R_FSO_2)_3CLi$ when $R_F$ is $CF_3$ cannot be simply extrapolated to the corresponding compounds in which $R_F$ is F. In fact, a compound $FSO_3Li$ is not stable in solution in a cyclic ether, in which it decomposes to give LiF and $SO_3$, thus causing a polymerization of the ether, in particular in the case of cyclic acetals. This compound was therefore absolutely not usable as salt in an ether. Consequently, it was not obvious that the improvement in the conductivity by the replacement of $CF_3SO_3Li$ (which is a usable salt, even though not the most effective one) by $(CF_3SO_2)_2NLi$ or $(CF_3SO_2)_3CLi$ could be transposed to the case of the replacement of $FSO_3Li$ (which is an unusable salt) by $(FSO_2)_2NLi$ or $(FSO_2)_3CLi$.

The inventors have found that ionically conductive materials exhibiting outstanding conductivity and stability properties can be obtained from ionic fluorine compounds which include at least one group in which a fluorine atom is bonded directly to a heteroatom.

An ionically conductive material of the present invention includes at least one ionic compound in solution in an aprotic solvent. It is characterized in that the ionic compound is chosen from the compounds represented by one of the formulae

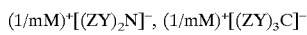

and

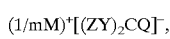

in which:

Y denotes $SO_2$ or POZ;

Q denotes —H, —COZ or Z;

each substituent Z independently denotes a fluorine atom or an optionally perfluorinated organic group which optionally contains at least one polymerizable functional group, at least one of the substituents Z denoting a fluorine atom;

M denotes a cation chosen from the proton and the cations derived from an alkali metal, an alkaline-earth metal, a transition metal, zinc, cadmium, mercury, a rare earth, or from diazonium ions, phosphonium ions, sulphonium ions or oxonium ions, or from the organic cations $NuR^+$, in which Nu is chosen from ammonia, alkylamines, pyridines, imidazoles, amidines, guanidines and alkaloids, and R denotes hydrogen, an alkyl group or an oxaalkyl group preferably containing from 1 to 20 carbon atoms or an aryl group preferably containing from 6 to 30 carbon atoms, the methyl, ethyl, propyl, lauryl and methoxyethyl groups being very particularly preferred.

The ionic compound employed for the preparation of the ionically conductive material preferably contains two substituents $FSO_2$—.

While the publications of the prior art suggested that the replacement of a perfluoroalkyl group by a fluorine atom in a salt caused a decrease in the dissociation of the said salt and while, furthermore, an F—S bond was less stable than a C—F bond, everything else being identical, the inventors have surprisingly found that the ionic compounds employed in the ionically conductive materials of the present invention exhibit a high stability, both chemical and electrochemical, in aprotic media, despite the existence of S—F bonds. Consequently, such compounds exhibit a wide range of stability towards oxidation-reduction phenomena. Furthermore, the conductivity of these ionic compounds in solution in aprotic solvents or in solvating polymers or in mixtures thereof is at least comparable, or even superior to those of the ionic compounds employed conventionally or to those of the derivatives of $[R_FSO_2NSO_2R_F]^-$. In addition, the ionic compounds of the invention have a molecular mass which is lower than that of the corresponding perfluoroalkyl compounds and their preparation is more economic, since it starts with industrial products.

When the substituent Z is other than a fluorine atom, it may be chosen in order to impart to the ionic compound of the invention the additional property or properties with a view to its use. The choice, in the case of Z, is consequently very wide.

In general, Z may be chosen from $C_1$–$C_{30}$ alkyl or $C_1$–$C_8$ perhaloalkyl radicals, $C_6$–$C_{12}$ aryl or perhaloaryl radicals, arylalkyl radicals, oxaalkyl, azaalkyl, thiaalkyl radicals and heterocyclic rings. More particularly, when Z is an alkyl radical, an arylalkyl radical or a perhaloalkyl radical containing more than 4 carbon atoms, the ionic compound of the present invention exhibits surface-active properties.

When Z denotes a mesomorphic group the ionic compound of the invention exhibits the properties of a liquid crystal.

The polymerizable functional group of the substituent Z may be a functional group polymerizable, for example, by a radical route, by an anionic route or by a reaction of Vandenberg type.

When Z contains ethylenic unsaturations, for example —C=C—, —C=C—C=O, —C=$SO_2$— or —C=CΦ, the compound of the invention can be polymerized.

When Z contains at least one condensable functional group such as, for example, an —$NH_2$ group carried by an aromatic group, or an —OH or —COOH or —N=C=O group, the ionic compound of the invention can be incorporated into a network obtained by polycondensation.

When Z contains a dissociable group such as, for example, an —O—O— peroxide group, an —N=N diazo group, an $N_2$=CH— azo group, an —$SO_2N_3$ group or an S—S-disulphide group, the ionic compound of the invention can be employed as a radical initiator.

The group Z may consist of a polymeric chain. The ionic compound of the invention can then form a polyelectrolyte.

The group Z may be a hindered phenol or a quinone. The compound of the invention then forms a scavenger for free radicals and exhibits antioxidant properties.

When Z is a chromophore group, for example Rhodamine B, the ionic compound of the invention is a dye.

When Z contains a cyclic ester, nitrile or amide functional group, the ionic compound of the invention forms a dissociating dipole.

Z may also contain a redox couple such as, for example, a disulphide, a thioamide, a ferrocene, a phenothiazine, a bis(dialkylamino)aryl, a nitroxide or an aromatic imide.

Z may also be a doped or autodoped electronically conductive polymer.

Z may also form a complexing ligand or a zwitterion.

Z may furthermore be a hydrolysable alkoxysilane, an amino acid or an optically or biologically active polypeptide.

Z may also be chosen from the groups $R^3$—CFX—, $R^3$—O—$CF_2$—CFX—, $R^1R^2$N—CO—CFX— or $R^1R^2$N—$SO_2$—$(CF_2)_n$—CFX— with n=1, 2 or 3, in which:

X denotes F, Cl, H or $R_F$;

the radicals $R^1$, $R^2$ and $R^3$, which are identical or different, are chosen from polymerizable nonperfluorinated organic radicals;

$R_F$ is chosen from perfluoroalkyl radicals and perfluoroaryl radicals.

Among the $R_F$ groups of the perfluoroalkyl type preference is given to perfluoroalkyl radicals containing from 1 to 8 carbon atoms and more particularly perfluoroalkyl radicals containing from 1 to 4 carbon atoms. The radicals $CF_3$—, $C_2F_5$—, n—$C_3F_7$— and n—$C_4F_9$— may be mentioned.

Among the $R_F$ groups of the perfluoroaryl type preference is given to perfluoroaryl radicals containing from 6 to 8 carbon atoms, for example the perfluorophenyl radical.

The polymerizable nonperfluorinated organic groups $R^1$, $R^2$ and $R^3$ permit polymerization reactions by a radical, anionic, cationic or stereospecific route, or by polycondensation. They may be chosen from those which contain double bonds, for example double bonds of the vinyl, alkyl, vinylbenzyl or acryloyl type. They may also be chosen from those which contain oxirane or oxetane functional groups. Furthermore, they may be chosen from those which contain alcohol, thiol, arylamine, isocyanate or trialkoxysilane functional groups. They may also be chosen from those which contain functional groups permitting an electropolymerization.

An ionically conductive material of the present invention includes at least one ionic compound as described above and at least one aprotic solvent.

The solvent may be an aprotic liquid solvent chosen, for example, from linear ethers and cyclic ethers, esters, nitrites, nitro derivatives, amides, sulphones, sulpholanes and sulphamides. Solvents which are particularly preferred are diethyl ether, dimethoxyethane, tetrahydrofuran, dioxane, dimethyltetrahydrofuran, methyl or ethyl formate, propylene or ethylene carbonate, butyrolactones, acetonitrile, benzonitrile, nitromethane, nitrobenzene, dimethylformamide, diethylformamide, N-methylpyrrolidone, dimethyl sulphone, tetramethylene sulphone and tetraethylsulphonamide.

The solvent may also be chosen from optionally crosslinked solvating polymers optionally bearing grafted ionic groups. A solvating polymer is a polymer which includes solvating units containing at least one heteroatom chosen from sulphur, oxygen, nitrogen and fluorine. Examples of solvating polymers which may be mentioned are polyethers of linear, comb or block structure, optionally forming a network, based on poly(ethylene oxide), or copolymers containing the ethylene oxide or propylene oxide or alkyl glycidyl ether unit, polyphosphazenes, crosslinked networks based on polyethylene glycol crosslinked with isocyanates or the networks obtained by polycondensation and carrying groups which allow crosslinkable groups to be incorporated. Block copolymers in which some blocks carry functional groups which have redox properties may also be mentioned. Of course, the above list is not limitative and any polymers exhibiting solvating properties may be employed.

An ionically conductive material of the present invention may simultaneously include an aprotic liquid solvent chosen from the abovementioned aprotic liquid solvents and a solvating polymer solvent. It may include from 2 to 98% of liquid solvent.

The solvent of an ionically conductive material of the present invention may also consist essentially of a nonsolvating polar polymer including units containing at least one heteroatom chosen from sulphur, oxygen, nitrogen and fluorine, and of an aprotic liquid chosen from the abovementioned aprotic liquid solvents. An example of nonsolvating polar polymer which may be mentioned is a poly (acrylonitrile), a poly(fluorovinylidene) or a poly(N-vinylpyrrolidone). The proportion of aprotic liquid in the solvent may vary from 2% (corresponding to a plasticized solvent) to 98% (corresponding to a gelled solvent).

An ionically conductive material of the present invention may additionally contain a salt employed conventionally in the prior art for the preparation of an ionically conductive material. In such a case the ionic compound of the invention also acts as an additive for passivating the collector of the cathode, for example when the ionically conductive material is employed in a rechargeable lithium generator whose cathode has a collector made of aluminum. Among the salts which can be employed in a mixture with an ionic compound according to the invention very particular preference is given to a salt chosen from perfluoroalkanesulphonates, bis(perfluoroalkylsulphonyl)imides, bis (perfluoroalkylsulphonyl)methanes and tris (perfluoroalkylsulphonyl)methanes.

Of course, an ionically conductive material of the invention may additionally contain the additives employed conventionally in a material of this type, and especially a plasticizer, a filler, other salts, etc.

An ionic compound $(1/mM)^+[FSO_2NSO_2Z]^-$ of the present invention, in which Z denotes a fluorine atom or a perfluoroalkyl radical $R_F$, may be prepared by reacting the corresponding acid $[FSO_2NSO_2Z]H$ in an unreactive aprotic solvent with a salt of the cation M, which is chosen so as to form in the course of the reaction an acid which is volatile or insoluble in the reaction mixture and whose basicity is sufficiently low not to affect the S—F bond. In the particular case of a lithium compound the reaction may advantageously take place according to the following reaction scheme:

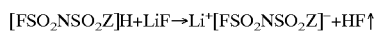
$[FSO_2NSO_2Z]H + LiF \rightarrow Li^+[FSO_2NSO_2Z]^- + HF\uparrow$

The aprotic solvent may be chosen from nitrites, nitroalkanes, esters and ethers. Acetonitrile is a solvent which is particularly preferred because of its volatility and its stability.

The salt employed for reacting with the starting acid and capable of releasing a volatile acid may be chosen from fluorides, chlorides, acetates and trifluoroacetates. Fluorides, which do not react with the fluorosulphonyl group and which produce the volatile acid HF, are particularly preferred.

The salt employed for reacting with the starting acid and which makes it possible to obtain an insoluble acid may be chosen from the salts of organic diacids or of polyacids by choosing a stoichiometry such that the product formed is an acid salt that is insoluble in aprotic solvents. Examples of such salts which may be mentioned are oxalates, malonates, polyacrylates, optionally crosslinked polymethacrylates, polyphosphates and zeolites.

Each of the compounds $(1/mM)^+[(ZY)_2N]^-$, $(1/M)^+[(ZY)_3C]^-$ and $(1/mM)+[(ZY)_2CQ]^-$ (in which Y denotes $SO_2$ or POZ and Q denotes —H, —COZ or Z, each substituent Z independently denoting a fluorine atom or an optionally perfluorinated organic group which optionally contains at least one polymerizable functional group, at least one of the substituents Z denoting a fluorine atom as defined above, M being as defined above) may be prepared by an analogous process from the corresponding acid $H[(ZY)_2N]$, $H[(ZY)_3C]$ or $H[(ZY)_2CQ]$.

The process described above for the preparation of the ionic compounds of the present invention is particularly advantageous insofar as it makes it possible to obtain the salts of small cations and especially the lithium salts which could not be obtained by the processes of the prior art. The lithium salts represented by the formulae $Li^+[(ZY)_2N]^-$, $Li^+[(ZY)_3C]^-$ and $Li^+[(ZY)_2CQ]^-$ (in which Y denotes $SO_2$ or POZ, Q denotes —H, —COZ or Z and each substituent Z independently denotes a fluorine atom or an optionally perfluorinated organic group which optionally contains at least one functional group polymerizable by a radical route, anionic route or by a reaction of Vandenberg type, at least one of the substituents Z denoting a fluorine atom), which could not be obtained by the processes of the prior art, consequently form another subject of the present invention.

An ionically conductive material of the present invention, containing at least one of the abovementioned ionic compounds $(1/mM)^+[(ZY)_2N]^-$, $(1/mM)^+[(ZY)_3C]^-$ and $(1/mM)^+[(ZY)_2CQ]^-$ (in which Y denotes $SO_2$ or POZ and Q denotes —H, —COZ or Z, each substituent Z independently denoting a fluorine atom or an optionally perfluorinated organic group which optionally contains at least one polymerizable functional group, at least one of the substituents Z denoting a fluorine atom as defined above, M being as defined above) in solution in an aprotic solvent can be employed as electrolyte in a lithium electrochemical generator. A lithium generator is intended to mean a generator in which the negative electrode contains lithium, it being possible for the negative electrode to consist of metallic lithium, a lithium alloy or else intercalated ionic lithium, for example $LiC_6$. In the two latter cases the generator is of the "rocking chair" type, in which each of the electrodes is a lithium intercalation compound.

The material may also be employed as electrolyte in a supercapacity. A supercapacity is an electrochemical system including an electrolyte and electrodes consisting of carbon or of another inert material of high specific surface, or else of a conjugated redox polymer of the polyacetylene, polyaniline or polythiophene type.

A material of the invention may also be employed for the p or n doping of an electronically conductive polymer. For example, a film of poly(3-phenylthiophene) is doped electrochemically in a solution of one of the ionic compounds $(1/mM)^+[(ZY)_2N]$, $(1/mM)^+[(ZY)_3C]^-$ and $(1/mM)^+[(ZY)_2CQ]^-$ (in which Y denotes $SO_2$ or POZ and Q denotes —H, —COZ or Z, each substituent Z independently denoting a fluorine atom or an optionally perfluorinated organic group which optionally contains at least one polymerizable functional group, at least one of the substituents Z denoting a fluorine atom as defined above, M being as defined above) in a liquid solvent and in a solvating polymer. The polymer thus doped may be employed as electrode material in a supercapacity such as mentioned above.

An ionically conductive material of the invention may also be employed in an electrochromic system.

An ionic compound of the invention may also be employed as a constituent of low-temperature molten electrolytes and especially of electrolytes which include a polymer enabling them to be endowed with plastic or elastomer properties. The ionic compounds of the invention in which the cation is a quaternary imidazolium are very particularly suited for this application.

The present invention is described in greater detail with the aid of the examples below, to which the invention is not, however, limited.

EXAMPLE 1

Preparation of lithium bis(fluorosulphonyl)imide

Bis(fluorosulphonimide) $(FSO_2)_2NH$ was prepared by distillation of fluorosulphonic acid in the presence of urea, reacting according to the reaction $$3HFSO_3 + CO(NH_2)_2 \rightarrow (FSO_2)_2NH + CO_2 + HF + (NH_4)HSO_4$$

All the operations were performed in an apparatus made of polymer which is resistant to the action of hydrofluoric acid. It would also be possible to employ an apparatus made of metal which is resistant to the action of hydrofluoric acid.

18 g of $(FSO_2)_2NH$ were dissolved in 80 ml of anhydrous acetonitrile and 5 g of lithium fluoride were added thereto. The mixture was stirred for 5 hours and then the suspension obtained was centrifuged. The lithium salt formed according to the reaction:

$$[FSO_2NSO_2F]H + LiF \rightarrow Li[FSO_2NSO_2F] + HF\uparrow$$

The solution was concentrated with the aid of a rotary evaporator and the salt was obtained in anhydrous form by treatment under primary vacuum.

Lithium bis(fluorosulphonyl)imide (LiFSI) is a white solid which is very soluble in aprotic solvents.

EXAMPLE 2

The LiFSI salt obtained in Example 1 was dissolved in a polyether and the electrolyte thus obtained was subjected to various measurements. The polyether employed is an ethylene oxide copolymer containing approximately 80% of ethylene oxide units. Such a copolymer is described, for example, in EP-A-0 013 199 or in U.S. Pat. No. 4,578,326. The salt concentration in the electrolyte was 1 mole of LiFSI per 30 moles of oxygen of the ether solvating units (O/Li=30/1).

Tests by differential scanning calorimetry (DSC) were performed with a view to testing the heat stability of the solid solution. During the DSC tests, the sample was heated successively to increasingly high temperatures for a few minutes, up to a maximum temperature of 160° C. FIG. 1 shows the DSC curves, labelled a), b) and c), obtained after exposure to 90° C., 140° C. and 160° C. respectively. The temperature T, expressed in ° C., is plotted as the abscissa; the heat flux HF, expressed in arbitrary units, is plotted as the ordinate. The three curves which, for convenience of reading, have been offset vertically relative to one another, have substantially the same appearance and indicate a glass transition temperature Tg of approximately −49° C.

Figure 2:
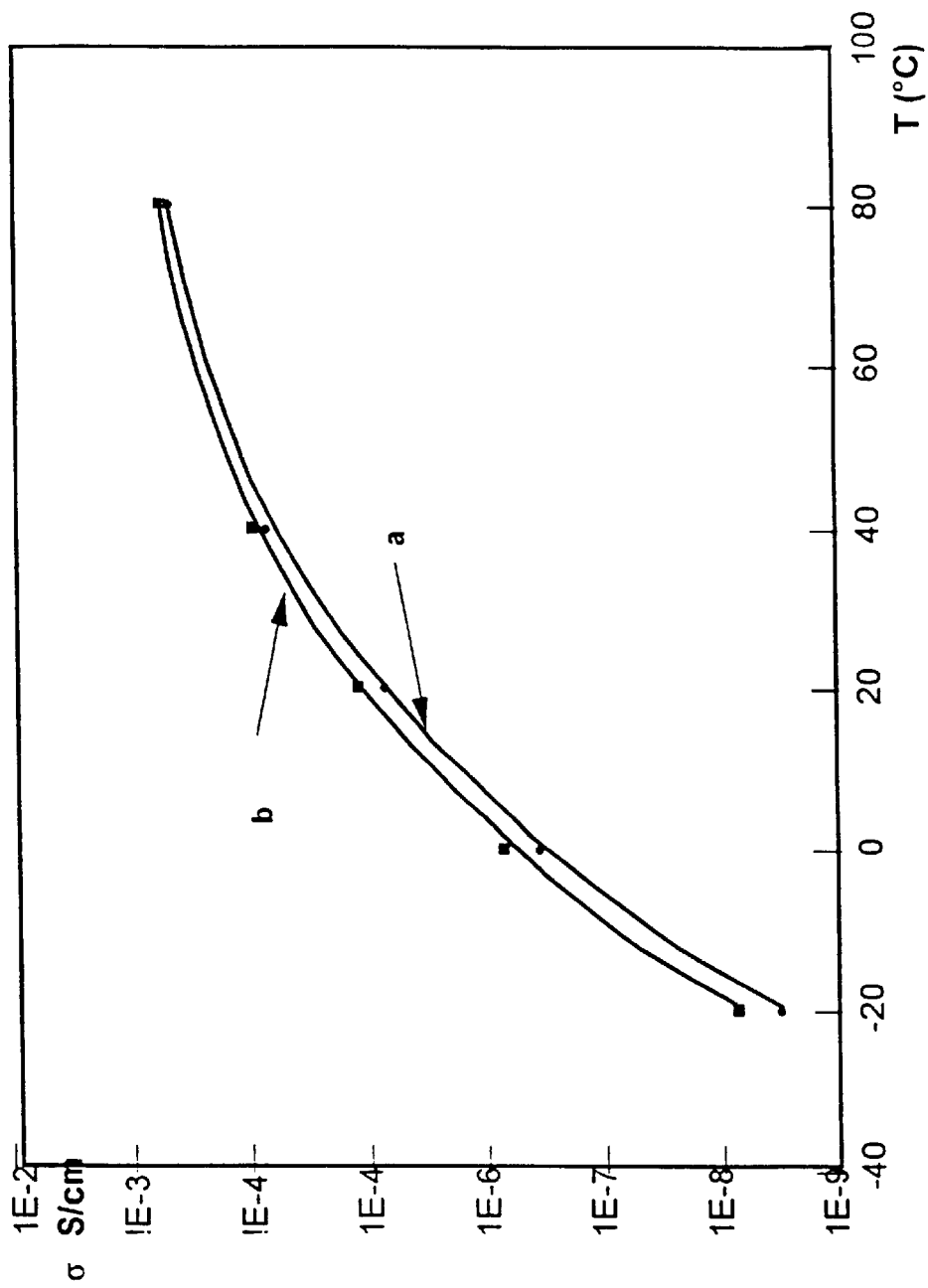

The conductivity of the electrolyte was determined by impedance measurement and was compared with that of a similar electrolyte in which the salt was a lithium trifluorosulphonylimide (LiTFSI). FIG. 2 shows the change in the conductivity σ, expressed in S cm$^{-1}$, as a function of the temperature T, for the electrolyte of the invention (curve a) and the comparative electrolyte (curve b) respectively. It appears that, at the salt concentration employed (O/Li=30/1), the conductivity of LiFSI is substantially equivalent to that of LiTFSI throughout the temperature range, which itself is known to be superior to that of lithium trifluoromethanesulphonate (lithium triflate).

These results demonstrate the heat stability of the salt of the invention in the form of polymer electrolyte. If the conductivity/molecular weight ratio is taken into account, it appears that it is highly advantageous to replace, in a lithium generator, all or part of the lithium salts available in the prior art, for example LiTFSI, lithium triflate or other, more toxic salts such as $LiAsF_6$, with the LiFSI salt of the invention.

EXAMPLE 3

The LiFSI salt was dissolved in propylene carbonate, employed as an aprotic solvent in most of the liquid-electrolyte generators and as an additive in some polymer electrolytes in order to increase their ionic conductivity.

Figure 3:
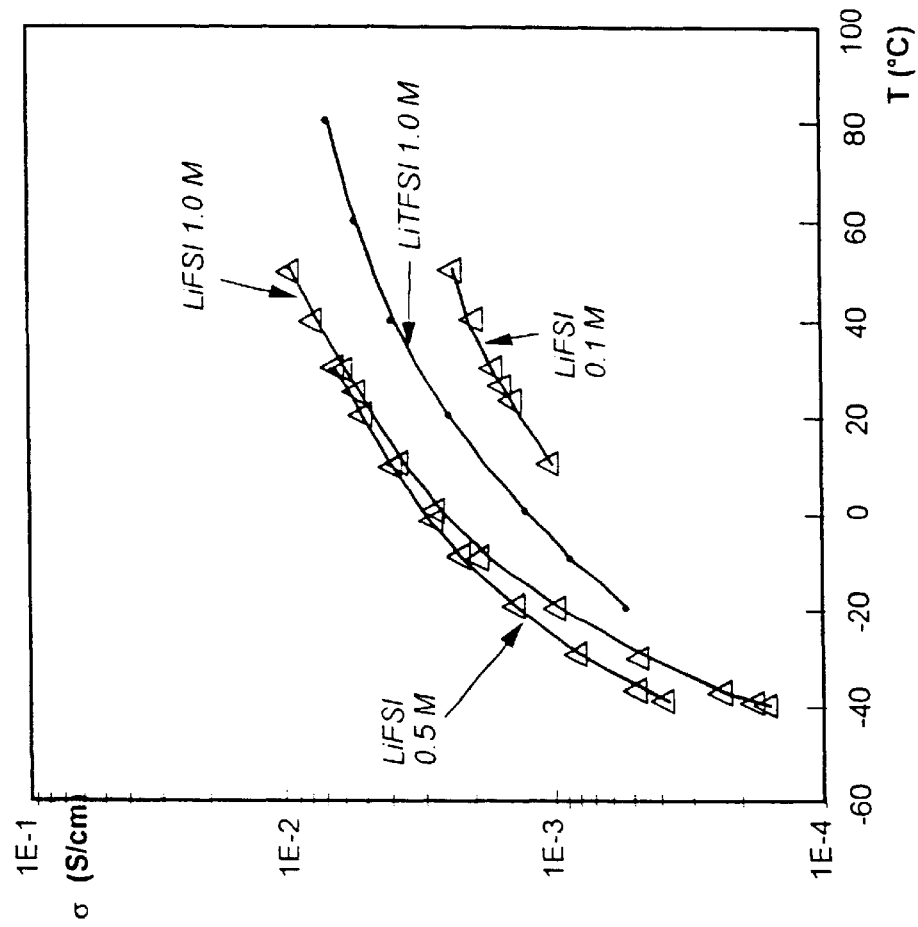

The change in the conductivity was measured as a function of temperature in the case of the following three concentrations of LiFSI salt: 1.0 molar, 0.5 molar and 0.1 molar. FIG. 3 shows the variation of the conductivity σ, expressed in S cm$^{-1}$, as a function of the temperature T for each of the concentrations and the variation of the conductivity at a concentration of 1.0 mole of LiTFSI salt by way of comparison.

The conductivity values determined, and especially the conductivity/molecular weight ratio of the LiFSI salt of the invention compare advantageously with those of the LiTFSI salt of the prior art and, thereby even more so, with those of lithium triflate, known to be less conductive than LiTFSI.

EXAMPLE 4

The electrochemical stability of the salt LiFSI was tested in a lithium rechargeable generator.

Three cells were tested for this purpose; they are of the type:

| Li° | polymer electrolyte | composite cathode based on vanadium oxide | nickel collector |
|-----|---------------------|-------------------------------------------|------------------|

Each of the cells consists of a lithium anode of 30-micron thickness, a polymer electrolyte of 30-micron thickness and a composite cathode containing approximately 40% of vanadium oxide, approximately 10% of acetylene black and approximately 50% of an ethylene oxide copolymer, the proportions being expressed by volume. The cathode, which has a capacity close to 5–6 C/cm$^2$ is coated onto a thin nickel collector. The cell has an active area of 3.89 cm$^2$. It was assembled by pressing with heating to 80° C.

In the case of cell No. 1 the electrolyte contains the salt LiFSI, the average salt concentration of LiFSI in the cell corresponding to an O/Li ratio of 54/1. The cell was cycled at constant currents (Id=450 μA, then 300 μA, and Ic=200 μA) between the limits of 3.3 and 1.5 volts.

The salt of the electrolyte in cell No. 2 is LiTFSI with an O/Li ratio=30/1. This cell was cycled at constant currents (Id=600 μA and Ic=200 μA) between the limits of 3.3 and 1.5 volts.

The salt of the electrolyte in cell No. 3 was LiFSI with an O/Li ratio of 30/1.

Figure 4:
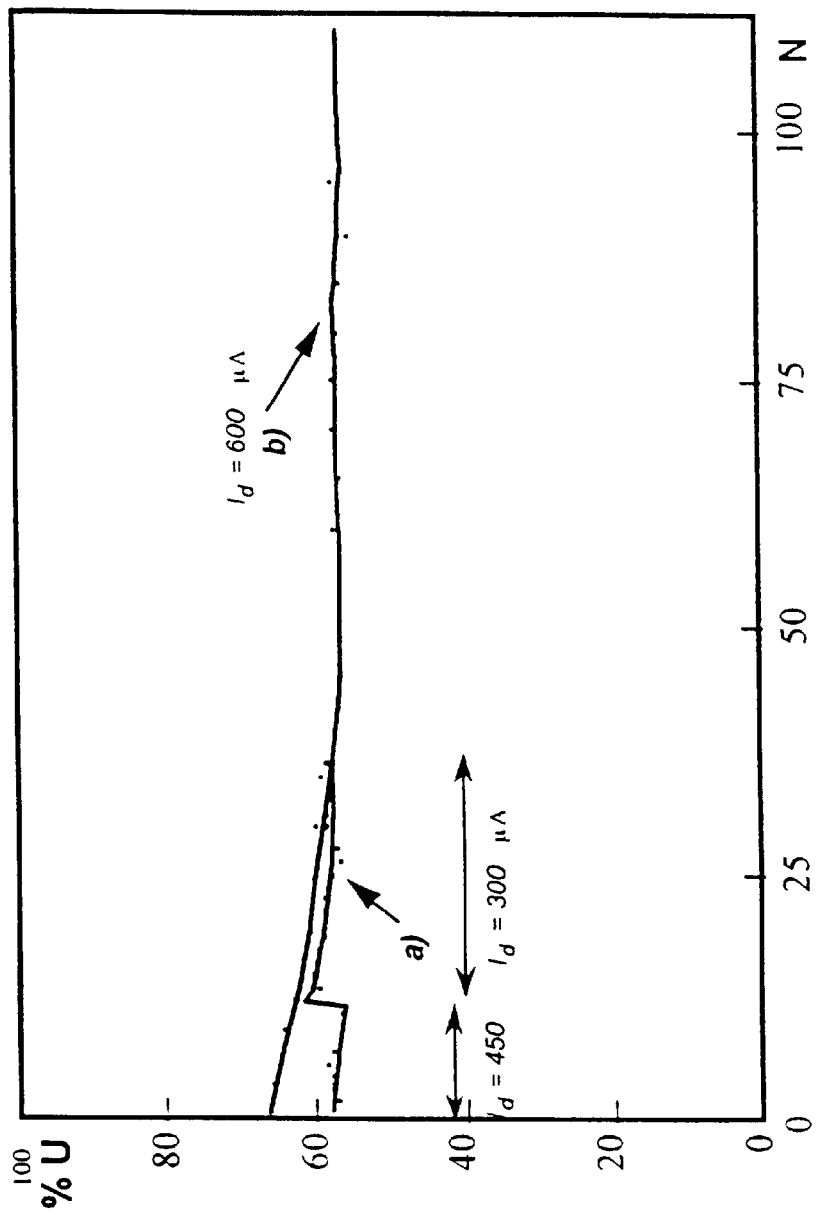

FIG. 4 shows the cycling curves of cells No. 1 and No. 2. The cycling curve gives the percentage utilization (% U) of the cathode (assuming 1 Li atom per vanadium atom) as a function of the number of cycles N.

The cycling curve of cell No. 1 (curve a in FIG. 4) is wholly comparable with that of cell No. 2 (curve b, FIG. 4) after 30 complete charge/discharge cycles and the slope of slow decrease in the utilization is substantially the same in both cases, within the accuracy of the experimental measurements. The initial degree of utilization of the cathode, slightly higher in the case of curve B) is the result of a higher salt concentration.

Cell No. 3 gives substantially the same results over 50 cycles, but exhibits a degree of utilization identical with that of curve b), obtained for cell No. 2 containing LiTFSI at the same concentration.

In all cases the initial impedance and the impedance after the cycling of the cells remain low and lower than 15 Ω after the cycling.

The tests, which were performed in demanding conditions, that is to say at 60° C. over several weeks, do confirm the thermal and electrochemical stability of the salt of the invention in the conditions of an electrochemical generator, that is to say in the absence of water and of chemical compounds capable of hydrolysing the salt. In fact, while the presence of residual impurities in the LiFSI salt employed could strictly have affected the absolute value of the conductivity measurements, the behaviour of the salt during the cycling establishes beyond doubt the compatibility of the salt and of the electrolytes produced according to the invention.

EXAMPLE 5

A lithium rechargeable cell was produced, in which the electrolyte contains a second salt (LiTFSI) in addition to a salt (LiFSI) of the invention.

The cell is of the type:

| Li$^0$ | polymer electrolyte | composite cathode based on vanadium oxide | aluminum collector |
|---|---|---|---|

Its characteristics are identical with those of the cells of Example 4, except for the collector which is aluminum in the present example.

The LiTFSI and LiFSI content is such that O/Li (total)= 30/1, and that the FSI/TFSI molar ratio is 8/100. The cycling performance of this cell was compared with that of an analogous cell containing only LiTFSI. Both cells were cycled at constant discharge and charge currents (Id=400 μA, Ic=225 μA) between the voltage limits of +3.3 and +1.5 volts.

Figure 5:
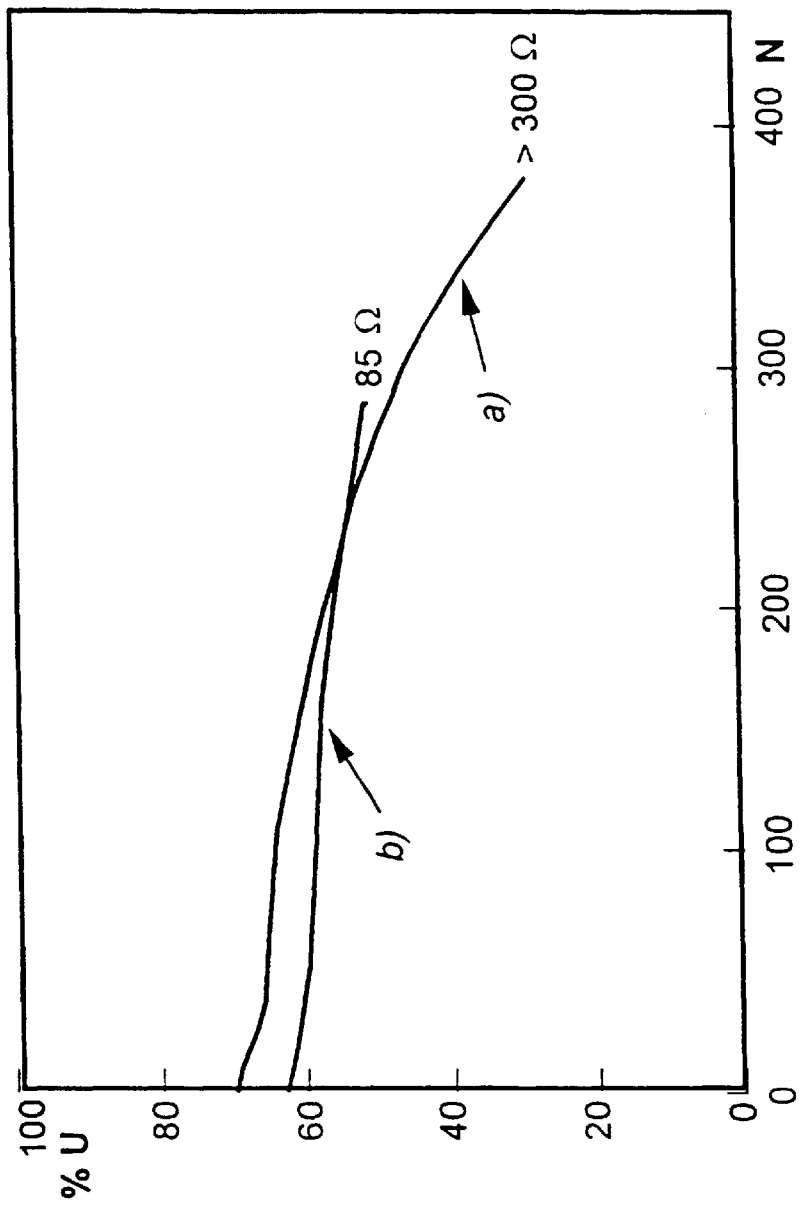

FIG. 5 shows the cycling curves of the two cells. The cycling curve gives the percentage utilization (% U) of the cathode (assuming 1 Li per V) as a function of the number of cycles N. Curve b) relates to the cell containing the mixture of salts and curve a) relates to the cell containing only LiTFSI. After nearly 300 deep discharge cycles at 60° C. the percentage utilization of the cathode is more stable and, above all, the impedance after cycling remains lower than 90 Ω for the cell in accordance with the invention, containing the mixture of salts, whereas the impedance of the cell containing only LiTFSI is higher than 300 Ω. It would therefore appear that the addition of LiFSI, in principle less stable than LiTFSI, to an electrolyte containing LiTFSI facilitates the formation of a fluorine-containing passivating film on the aluminum collector without impairing the conductivity. The film formed seems to be very thin, of the order of a few tens or a few hundred nanometres, because inspection with a scanning microscope (SEM) of the surface of the aluminum after cycling and washing does not show any significant attack of the surface of the aluminum, despite the difference which is observed between the impedance values for the two cells which are compared.

EXAMPLE 6

A lithium primary cell operating at the ambient temperature is produced, in which the electrolyte contains the salt (LiFSI) of the invention, and a polymer solvent similar to that of the preceding examples but plasticized by addition of propylene carbonate (PC).

The cell is of the type:

| Li$^0$ | polymer electrolyte + PC | composite cathode based on manganese oxide | aluminum collector |
|---|---|---|---|

The ratio of the number of moles of PC to the number of moles of lithium salt is PC/Li=5/1. The concentration of lithium salt in the electrolyte is such that O/Li=30/1. The cell exhibits an open-circuit voltage (OCV) which is very stable as a function of time for more than a fortnight, which confirms the absence of self-discharge or of secondary reactions.

When the cell is discharged at a constant current of 78 μA with a lower voltage limit of +2.0 volts, the discharge curve exhibits a regular plateau typical of a cathode of MnO$_2$ type, the mean voltage of which is 2.8 volts. The percentage utilization (assuming 1 Li per Mn) of the cathode of this cell, which has a capacity of 5.69 C/cm$^2$ and an area of 3.86 cm$^2$ represents 75% of the active material. The result confirms the electrochemical compatibility of the salts of the invention in the presence of a liquid electrolyte, employed in this case in the form of a plasticizer of a polymer electrolyte.

The cost, electrical conductivity and molecular mass factors associated with the salts of the present invention therefore offer considerable advantages over the known salts employed in the prior art in lithium or sodium generators. These advantages are valid equally well in the case of the liquid electrolytes and in the case of the polymer electrolytes, whether plasticized or not, and in the case of the generators using metallic or alloy anodes or of the generators of the "rocking chair" type, in particular generators of the lithium ion type like, for example, those employing LiC$_6$.

What is claimed is:

1. A compound having one of the formulae $$Li^{\oplus}[(ZSO_2)_2N]^{\ominus}, \; Li^+[(ZSO_2)_3C]^{\ominus}$$

or $$Li^{\oplus}[(ZSO_2)_2CQ]^{\ominus},$$

wherein:

Q is —H, —COZ or Z; and each substituent Z independently is a fluorine atom or an optionally perfluorinated organic group which optionally contains at least one polymerizable functional group, at least one of the substituents Z being a fluorine atom.

2. The compound of claim 1, wherein at least two substituents Z are a fluorine atom.

3. The compound of claim 1, wherein each substituent Z other than F of the ionic compound is independently $C_1$–$C_{20}$ alkyl or $C_1$–$C_8$ perhaloalkyl radicals, $C_6$–$C_{12}$ aryl or perhaloaryl radicals, arylalkyl radicals, oxaalkyl, azaalkyl, thiaalkyl radicals or heterocyclic rings.

4. The compound of claim 1, wherein each substituent Z other than F of the ionic compound is independently radicals which contain at least one ethylenic unsaturation or a condensable group or a dissociable group.

5. The compound of claim 1, wherein each substituent Z other than F of the ionic compound independently is a mesomorphic group or a chromophore group or a doped or autodoped electronic conductor polymer or a hydrolysable alkoxysilane.

6. The compound of claim 1, wherein each substituent Z other than F of the ionic compound independently forms a polymeric chain.

7. The compound of claim 1, wherein each substituent Z other than F of the ionic compound independently a group which contains a scavenger for free radicals comprising a hindered phenol or a quinone; or a dissociating dipole comprising an amide or a nitrile; or a redox couple comprising a disulphide, a thioamide, a ferrocene, a phenothiazine, a bis(dialkylaminoaryl) group, a nitroxide, or an aromatic imide; or a complexing ligand or a zwitterion.

8. The compound of claim 1, wherein each substituent Z other than F of the ionic compound is independently $R^3$—CFX—, $R^3$—O—$CF_2$—CFX—, $R^1R^2B$—CO—CFX—, or $R^1R^2N$—$SO_2$—$(CF_2)_n$—CFX— wherein n=1, 2 or 3, in which:

X is F, Cl, H or $R_F$;

the radicals $R^1$, $R^2$ and $R^+$, which are identical or different, are polymerizable nonperfluorinated organic radicals; and $R_F$ is a perfluoroalkyl radical or perfluoroaryl radical.

9. The compound of claim 8, wherein the radical $R_F$ is a perfluoroalkyl radical containing from 1 to 8 carbon atoms or a perfluoroaryl radical containing from 6 to 8 carbon atoms.

10. The compound of claim 8, wherein the polymerizable nonperfluorinated organic groups $R^1$, $R^2$ and $R^3$ are organic radicals containing double bonds or radicals containing oxirane or oxetane functional groups or radicals containing alcohol, thio, arylamine, isocyanate or trialkoxysilane functional groups or radicals containing functional groups permitting electropolymerization.

11. The compound of claim 1, wherein the polymerizable functional group of a substituent Z other than F is a functional group which is radically polymerizable, anionically polymerizable or polymerizable by a Vanderberg reaction.

12. The compound of claim 1, which is anhydrous.

13. A compound having by one of the formulae $$1/mM^{\oplus}[(ZSO_2)_2N]^{\ominus}, \; 1/mM^{\oplus}[(ZSO_2)_3C]^{\ominus} \text{ or } 1/mM^{\oplus}[(ZSO_2)_2CQ]^{\ominus},$$

in which:

Q is —H, —COZ, $SO_2Z$ or Z;

each substituent Z independently is a fluorine atom or an optionally perfluorinated organic group which optionally contains at least one polymerizable functional group, at least one of the substituents Z being a fluorine atom;

M is a cation selected from the group consisting of an alkali metal different from $Li^{\oplus}$, an alkaline-earth metal, a transition metal, zinc, cadmium, mercury, a rare earth, diazonium ion, phosphonium ion, sulphonium ion, oxonium ion, and an organic cation $NuR^{\oplus}$, in which Nu is selected from the group consisting of ammonia, alkylamines, pyridines, imidazoles, amidines, guanidines and alkaloids, wherein R is hydrogen, an alkyl group or an oxaalkyl group containing from 1 to 20 carbon atoms or an aryl group containing from 6 to 30 carbon atoms; at least one substituent Z being an organic group which contains a functional group when M is an alkali metal other than Li or an alkaline earth metal; and m is the valency of the cation M.

14. The compound of claim 13, wherein at least two substituents Z are a fluorine atom and M is different from an alkali metal or an alkaline-earth metal.

15. The compound of claim 13, wherein each substituent Z other than F of the ionic compound is independently $C_1$–$C_{30}$ alkyl or $C_1$–$C_8$ perhaloalkyl radicals, $C_6$–$C_{12}$ aryl or perhaloaryl radicals, arylalkyl radicals, oxaalkyl, azaalkyl, thiaalkyl radicals or heterocyclic rings.

16. The compound of claim 13, wherein each substituent Z other than F of the ionic compound is independently radicals which contain at least one ethylenic unsaturation or a condensable group or a dissociable group.

17. The compound of claim 13, wherein each substituent Z other than F of the ionic compound independently is a mesomorphic group or a chromophore group or a doped or autodoped electronic conductor polymer or a hydrolyszable alkoxysilane.

18. The compound of claim 13, wherein each substituent Z other than F of the ionic compound independently forms a polymeric chain.

19. The compound of claim 13, wherein each substituent Z other than F of the ionic compound independently is a group which contains a scavenger for free radicals comprising a hindered phenol or a quinone; or a dissociating dipole comprising an amide or a nitrile; or a redox couple comprising a disulphide, a thioamide, a ferrocene, a phenothiazine, a bis(dialkylaminoaryl) group, a nitroxide, or an aromatic imide; or a complexing ligand; or a zwitterion.

20. The compound of claim 13, wherein each substituent Z other than F of the ionic compound is independently $R^3$—CFX—, $R^3$—O—$CF_2$—CFX—, $R^1R^2N$—CO—CFX—, or $R^1R^2N$—$SO_2$—$(CF_2)_n$—CFX— wherein n=1, 2 or 3 in which:

X is F, Cl, H or $R_F$; and the radicals $R^1$, $R^2$ and $R^+$, which are identical or different, are polymerizable nonperfluorinated organic radicals; and $R_F$ is chosen from perfluoroalkyl radicals and perfluoroaryl radicals.

21. The compound of claim 20, wherein the radicals $R_F$ are perfluoroalkyl radicals containing from 1 to 8 carbon atoms or perfluoroaryl radicals containing from 6 to 8 carbon atoms.

22. The compound of claim 20, wherein the polymerizable nonperfluorinated organic groups $R^1$, $R^2$ and $R^3$ are organic radicals containing double bonds or radicals containing oxirane or oxetane functional groups or radicals containing alcohol, thiol, arylamine, isocyanate or trialkoxysilane functional groups or radicals containing functional groups permitting an electropolymerization.

23. The compound of claim 13, wherein the polymerizable functional group or a substituent Z other than F is a functional group which is radically polymerizable, anionically polymerizable or polymerizable by a Vandenberg reaction.

24. The compound of claim 13, which is anhydrous.

25. An ion conduction material, which comprises at least one ionic compound in an aprotic solvent, wherein the ionic compound has one of the formula $$(1/mM)^{\oplus}[(FSO_2)_2N]^{\ominus}, (1/mM)^{\oplus}[(FSO_2)_3C]^{\ominus}$$

and $$(1/mM)^{\oplus}[(FSO_2)_2CQ]^{\ominus},$$

wherein:

Q is —H, —COZ or Z;

each substituent Z independently is a fluorine atom;

M is a cation selected from the group consisting of an alkali metal, an alkalino-earth metal a transition metal, zinc, cadmium, mercury, a rare earth, diazonium ion, phosphonium ion, sulphonium ion, oxonium ion, and an organic cation NuR$^+$, in which Nu is selected from the group consisting of ammonia, alkylamines, pyridines, imidazoles, amidines, guanidines, and alkaloids, wherein R is hydrogen, an alkyl group or an oxaalkyl group containing from 1 to 20 carbon atoms or an aryl group containing from 6 to 30 carbon atoms; and m is the valency of the cation M.

26. The ion conduction material of claim 25, wherein the solvent is an aprotic liquid solvent comprising linear ethers, cyclic ethers, esters, nitrites, nitro derivatives, amides, sulphones, sulphonates or sulphamides or a mixture thereof.

27. The ion conduction material of claim 25, wherein the solvent is optionally crosslinked solvating polymer optionally carrying grafted ionic groups.

28. The ion conduction material of claim 27, wherein the solvating polymer is selected from the group consisting of:

polyethers of linear, comb or block structure, optionally forming a network, based on poly(ethylene oxide), copolymers containing ethylene oxide or propylene oxide or alkyl glycidyl ether unit, polyphosphazenes, crosslinked networks based on polyethylene glycol crosslinked with isocyanates, networks obtained by polycondensation and bearing groups which allow the incorporation of crosslinkable groups, and block copolymers in which some blocks carry functional groups which have redox properties.

29. The ion conduction material of claim 25, wherein the solvent is a mixture of an aprotic liquid solvent and of a solvating polymer solvent.

30. The ion conduction material of claim 25, wherein the solvent consists essentially of an aprotic liquid solvent and a nonsolvating polar polymer solvent including units containing at least one heteroatom selected from the group consisting of sulphur, oxygen, nitrogen, and fluorine.

31. The ion conduction material of claim 29, wherein the nonsolvating polar polymer is selected from the group consisting of a poly(acrylonitrile), a poly(fluorovinylidene) and a poly(N-vinylpyrrolidone).

32. The ion conduction material of claim 25, which further comprises at least one second salt.

33. The ion conduction material of claim 32, wherein the second salt is selected from the group consisting of perfluoroalkanesulphonates, bis(perfluoroalkylsulphonyl)imides, bis(perfluoroalkyl-sulphonyl)methanes, tris(perfluoroalkylsulphonyl)methanes and their homologues thereof in which at least one sulphonyl group is replaced by a carbonyl group.

34. The ion conduction material of claim 25, which further comprises a plasticizer or a filler or both.

35. A process for preparing of a compound having one of the formulae $$(1/mM)^{\oplus}[(FSO_2)_2N]^{\ominus}, (1/mM)^{\oplus}[(FSO_2)_3C]^{\ominus} \text{ or } (1/mM)^{\oplus}[(FSO_2)_2CQ]^{\ominus}, \text{ in which:}$$

Q—s—H, —COZ or Z;

M is a cation selected from the group consisting of Li$^{\ominus}$, a transition metal, zinc, cadmium, mercury, a rare earth, diazonium ion, phosphonium ion, sulphonium ion, oxonium ion, and an organic cation NuR$^+$, in which Nu is selected from the group consisting of ammonia, alkylamines, pyridines, imidazoles, amidines, guanidines and alkaloids, wherein R is hydrogen, an alkyl group or an oxaalkyl group containing from 1 to 20 carbon atoms or an aryl group containing from 6 to 30 carbon atoms; and m is the valency of the cation M, which process comprises reacting a corresponding acid selected from the group consisting of H[(FSO$_2$)$_2$N], H[(FSO$_2$)$_3$C] or H[(FSO$_2$)$_2$CQ], respectively, in an unreactive aprotic solvent, with a salt of the cation M which is selected so as to form in the course or the reaction, a volatile acid or an acid which is insoluble in the reaction mixture and whose basicity is sufficiently weak not to affect the S—F.

36. The process of claim 35, wherein the aprotic solvent is selected from the group consisting of nitrites, nitroalkanes, esters and ethers.

37. The process of claim 35, wherein the salt employed for reacting with the corresponding acid and which forms a volatile acid is selected from the group consisting of fluorides, chlorides, acetates and trifluoroacetates.

38. The process of claim 35, wherein the salt employed for reacting with the corresponding acid and which forms an insoluble acid is selected from the group consisting of salts of organic diacids or polyacids, by choosing a stoichiometry whereby the product formed is an acid which is insoluble in aprotic solvents.

39. The process of claim 38, wherein the salt is selected from the group consisting of oxalates, malonates, polyacrylates, polymethacrylates, crosslinked polymethacrylates, polyphosphates and zeolites.

* * * * *